United States Patent [19]

Paradis et al.

[11] 4,231,943

[45] Nov. 4, 1980

[54] MALEIC ANHYDRIDE PRODUCTION

[75] Inventors: Stephen G. Paradis, Fairfax; David M. Marquis, Lafayette, both of Calif.; Kiran R. Bakshi, Murrysville, Pa.

[73] Assignee: Chevron Research Company, San Francisco, Calif.

[21] Appl. No.: 44,781

[22] Filed: May 31, 1979

Related U.S. Application Data

[63] Continuation-in-part of Ser. No. 645,585, Dec. 31, 1975, abandoned.

[51] Int. Cl.$^3$ .......................................... C07D 307/60
[52] U.S. Cl. ................................................ 260/346.75
[58] Field of Search .................................... 260/346.75

[56] References Cited

U.S. PATENT DOCUMENTS

| | | | |
|---|---|---|---|
| 3,741,993 | 6/1973 | Hughes | 260/346.75 |
| 3,856,824 | 12/1974 | Raffelson et al. | 260/346.75 |
| 3,904,652 | 9/1975 | Frank | 260/346.75 |

OTHER PUBLICATIONS

Bissot et al., I. and E. C. Product Research and Development, vol. 2(1) Mar. 1963, pp. 57–60.

*Primary Examiner*—Henry R. Jiles
*Assistant Examiner*—Bernard Dentz
*Attorney, Agent, or Firm*—D. A. Newell; T. G. DeJonghe; A. T. Bertolli

[57] ABSTRACT

A process for producing maleic anhydride from n-butane which comprises:
 (a) feeding n-butane and air to a reactor;
 (b) contacting the butane and air with a catalyst comprising vanadium and phosphorus oxides at reaction conditions including a temperature between 550° F. and 1000° F. so as to convert 15 to 28% of the butane per pass and obtain a reactor effluent containing maleic anhydride, unreacted butane, nitrogen, and oxygen;
 (c) removing maleic anhydride from the reactor effluent to obtain maleic anhydride-lean effluent;
 (d) recycling a portion of the maleic anhydride-lean effluent to the reactor;
 (e) removing butane from the other portion of the maleic anhydride-lean effluent; and
 (f) recycling the removed butane to the reactor.

Preferably the temperature in, and/or space velocity through, the reactor is adjusted to obtain a weight percent selectivity to maleic anhydride of at least 90% of the butane converted.

5 Claims, 2 Drawing Figures

MALEIC ANHYDRIDE PRODUCTION

CROSS-REFERENCE TO RELATED APPLICATION

This application is a continuation-in-part of application Ser. No. 645,585, filed Dec. 31, 1975 now abandoned.

BACKGROUND OF THE INVENTION

The present invention relates to the oxidation of a butane feed to maleic anhydride.

Oxidation of hydrocarbons to maleic anhydride is well known. Feeds which have been disclosed include benzene, butene, and n-butane. A series of patents to Kerr, including U.S. Pat. Nos. 3,156,705; 3,156,706; 3,156,707; 3,238,254; 3,255,211; 3,255,212; 3,255,213; 3,288,721; 3,351,565 and 3,385,796, discloses vanadium-phosphorus oxide catalysts for oxidation of butene to maleic anhydride.

Friedrichsen et al U.S. Pat. No. 3,478,063 discloses oxidation of olefinically unsaturated hydrocarbons with a catalyst containing vanadium and phosphorus oxides and wherein the amount of phosphorus oxide is at least equal to twice that of the vanadium oxide and wherein the catalyst contains at least one other oxide of chromium, iron, cobalt or nickel, and the catalyst is preferably on a carrier. The patent discloses at Col. 4 that the catalyst may have a surface area from 1 to 100 $m^2/g$.

Bergman U.S. Pat. No. 3,293,268 discloses a vanadium-phosphorus oxide catalyst for oxidation of butene to maleic anhydride. Surface area is not disclosed for the catalyst in the Bergman reference. Also, as in the Friedrichsen et al reference, the Bergman catalyst is prepared by an aqueous solution method.

Schneider U.S. Pat. No. 3,864,280 discloses a vanadium-phosphorus mixed oxide catalyst having an intrinsic surface area of 7 to 50 $m^2/g$. The Schneider catalyst can be prepared using an organic medium as opposed to an aqueous medium.

The use of recycle of unreacted constituents to a reactor is, of course, well known and frequently is employed in various processes. For example, in the oxidation of ethylene to ethylene oxide, ethylene and air are mixed with recycle gas containing mainly nitrogen and unconverted ethylene, and the mixture is passed over the catalyst. The catalyst is typically contained in tubes in a heat exchanger-type reactor with a boiling cooling fluid on the outside of the tubes to absorb the heat of reaction and control the temperature. Typically the catalyst for the ethylene oxidation is silver oxide on a refractory support, and typical operating conditions include a temperature in the range 392° F. to 572° F. and a pressure of 10 to 30 atmospheres.

Bissot et al, in "Oxidation of Butane to Maleic Anhydride", IEC Vol. 2, No. 1, March 1963, pp. 57-60, disclose that, in a process for conversion of butane to maleic anhydride unreacted butane may be recycled to the reactor. However, Bissot et al prefer to use sequential reaction, with maleic anhydride separation between the reactors, and with unreacted butane from the first reactor being fed to the second reactor, etc.

U.S. Pat. No. 3,904,652 discloses the oxidation of n-butane to maleic anhydride using enriched oxygen and with a recycle stream of reactor effluent which lowers the oxygen concentration in the total feed to the reactor. It is known that explosive mixtures of butane and oxygen exist and that some oxygen concentrations can cause an oxygen-butane-nitrogen mixture to go into the explosive range; see, for example, Bureau of Mines Bulletin 503 (1952), FIG. 35, page 62, and Bureau of Mines Bulletin 627 (1965), FIG. 21, page 23. In U.S. Pat. No. 3,904,652, the reactor feed mixture is kept below explosive (flammable) limits by the addition of an inert gas, e.g., nitrogen, to the enriched oxygen fresh feed.

Butane conversion levels in U.S. Pat. No. 3,904,652 are 30 to 70% per pass. The unconverted butane passes out of the oxidizer reactor as part of the reactor effluent. The effluent is processed to remove maleic anhydride. The maleic anhydride-free effluent is then divided into two parts, a recycle stream which is recycled back to the reactor, and a purge stream which is removed from the system. According to this patent, the oxygen level in the fresh feed is not desired to be below 50%; lower levels are not desired, according to the patent, as the lower levels would require increasing the amount of purge gas to be withdrawn from the recycle stream and hence would increase the unreacted butane loss in the process of said Patent.

SUMMARY OF THE INVENTION

According to the present invention a process is provided for producing maleic anhydride from n-butane which comprises:

(a) feeding n-butane and air to a reactor;

(b) contacting the butane and air with a catalyst comprising vanadium and phosphorus oxides at reaction conditions including a temperature between 550° and 1000° F. so as to convert or transform 15 to 28% of the butane per pass and obtain a reactor effluent comprising unreacted butane, nitrogen and maleic anhydride;

(c) removing maleic anhydride from the reactor effluent to obtain maleic anhydride-lean effluent;

(d) recycling a portion of the maleic anhydride-lean effluent to the reactor;

(e) removing butane from the other portion of the maleic anhydride-lean effluent; and (f) recycling the removed butane to the reactor.

Preferably the temperature in, and/or space velocity through, the reactor is adjusted to obtain a weight percent selectivity of at least 75%, more preferably at least 90% of the butane converted.

The term "conversion", as well as such terms as "selectivity" and "yield" are used herein in their general conventional processing sense. See, for example, "Chemical Process Principles", Part I, Second Edition, published by John Wiley & Sons, Inc., New York, particularly page 215.

Thus, the term "conversion" means the percentage of butane in the feed that is transformed, changed, or disappears. On a per-pass basis, it is the percentage of butane fed to the reactor. On a butane recycle or overall basis it is the percent of make-up or net butane fed to the process. The overall conversion is thus a function of both the amount of butane that is recycled, and the per pass conversion.

The term "selectivity" means the quantity of maleic anhydride produced, expressed as a percentage, by weight, of the total quantity of butane that is converted. On an overall basis, it is the quantity, by weight, of maleic anhydride attributable to make-up butane in the feed.

The term "yield" means the quantity of maleic anhydride produced, expressed as a percentage, by weight, of the butane fed to the reactor. On an overall basis, it is the net quantity of maleic anhydride product, expressed as a percentage, by weight, of the make-up butane feed. It may also be expressed as selectivity times the conversion, either on an overall or per pass basis.

Among other factors, the present invention is based on our findings that the use of the specified conversion levels (percent of the butane feed converted per pass) of the process of the present invention results in unexpectedly long run lengths of high selectivity and activity for the catalyst. We have found that the process is especially attractive by virtue of the integration of the specified conversion level, and the use of a recycle wherein a purge stream is treated for butane recovery and recycle of the butane to the process, and wherein air is used as the source of oxygen for the oxidation reaction.

Related to the above factors, particularly the finding of improved run length of high selectivity, is the supportive finding that there is a substantial lowering and flattening of the temperature profile curve for operation in accordance with the present invention at per pass conversions between 15 and 28%, for example at about 25%, versus conversions at higher levels such as 35%. This lowering and flattening of the temperature profile is explained in more detail with respect to FIG. 2. The temperature profile represents the temperatures along the length of the reactor tubes starting from the inlet of the feed gas to the tubes and proceeding to the outlet portion of the tubes.

Thus, compared to prior art processes, we have found that using the conversion levels of the present invention enables the butane recycle process to be operated at lower temperature and for longer catalyst run life for a given productivity (productivity is the pounds of maleic anhydride produced per unit time per volume of catalyst) in a recycle process using air as the oxygen source, particularly when the oxygen in the reaction zone feed is maintained at about 6–12 volume percent as well as the conversion being maintained within the stipulated levels. In the process of the present invention the oxygen concentration should be kept below the explosive level.

It is to be appreciated that as the conversion per pass is dropped, more butane needs to be fed to the reactor per unit time in order to maintain a given productivity, and that the increase in the butane concentration is a factor which tends to raise the catalyst bed hot spot temperature because the oxidation of butane is an exothermic reaction. However, through our experimental data, we have found that for a given productivity the process of the present invention generally operates at a lower temperature than would be the case for the same productivity on a once-through operation or for recycle operation at higher per pass conversion.

Particularly preferred butane per pass conversion levels for the process of the present invention have been found to be below 30%, and above 1 or 2% for example in the range of 20 to 28%, and especially preferred levels have been found to be 22 to 27% of n-butane oxidized to maleic anhydride and by-products per pass through the reactor.

Preferred operating conditions are as follows:

| | Preferred | More Preferred | Most Preferred |
|---|---|---|---|
| Temperature, °F. | 650–950 | 700–850 | 700–800 |
| Pressure, psig | 10–1000 | 20–50 | 25–40 |
| Space rate, VHSV[1] | 1000–10,000 | 2000–5000 | 3500–4500 |

| | Preferred | More Preferred | Most Preferred |
|---|---|---|---|
| Feed n-butane content, combined fresh + recycle feed. vol. % | 1–5 | 1.5–4 | 2–3.5 |
| % effluent recycled directly (remainder of effluent n-butane recycled after separation from other effluent gases) | 20–95 | 65–90 | 80 |

[1] Total volume of gas at 70° F. and 1 atm. per hour per cubic foot of catalyst volume The purge portion of the effluent recycle is treated for n-butane recovery for example by cryogenic cooling to selectively condense out the butane or by absorption of the butane in a solvent selective for butane absorption, but preferably by adsorption of n-butane onto a solid adsorbent selective for n-butane adsorption followed by a separate desorption step to recover a relatively pure stream of n-butane from the adsorbent. Preferred adsorbents are those wherein the adsorbent is an activated carbon adsorbent having a low affinity for polar compounds such as water and carbon dioxide. Particularly preferred adsorbents are activated carbon produced from coal, especially from bituminous coal, and having a high surface area between about 400 and 1500 m$^2$/g, preferably with a large percent (about 25% or more) of the pore volume coming from pores of 15–30 Angstroms in radius, and also preferably of small Tyler mesh size (about 4–60 mesh size).

A preferred cyclic adsorption-desorption system for the recovery of n-butane from the purge stream consists of 3 stages: adsorption, desorption, and cooling (with drying when steam is used for desorption). To provide a cycle for repetitive operation using multiple beds, the adsorption time desirably is equal to the total time for desorption and cooling. Adsorption is performed at as low a temperature as practical, usually in the range of 60–200° F., and at superatmospheric pressure. The time required for saturation of the adsorbent depends on these conditions in addition to the concentration of butane in the gas and the size of the carbon bed relative to the amount of gas to be processed. The time may be as short as ¼ hour or as long as 12 hours. Desorption of the n-butane can be accomplished in a variety of ways, depending on the form in which it is desired to be recovered.

Thus, it can be desorbed by use of a heated inert gas, e.g., $N_2$ or $CO_2$, or mixtures of these gases with air to provide a gaseous mixture suitable for recycle to the catalytic reactor. Alternatively, desorption can be carried out with low-pressure steam (15–100 psig), followed by condensation and separation of liquid C. and water layers in the usual manner. The liquid C. can then be returned to the plant feed inventory.

After desorption with heated gas (either fixed or condensable), the adsorption bed can be dried with inert hot gas, such as hot $N_2$ or $CO_2$, and cooled before starting the cycle again. Cooling can be accomplished by any of several means, e.g., by circulating a cold fluid through cooling coils imbedded in the carbon, by passing a cooled gas through the bed, or by a combination of these. The method chosen is dependent on the rate of cooling desired. We have found it advantageous to use the spent gas from another bed, operating on the adsorption cycle, to do the cooling. Alternatively, drying and cooling can be achieved in a combined step.

Spent carbon may require periodic regeneration to regain its adsorption capacity. Preferred regeneration operation is an in-situ treatment of the carbon by hot flue gases at 400–1000° F.

According to a particularly preferred embodiment of the present invention, the butane is recycled to "extinction," i.e., all the butane fed to the process is ultimately converted by way of recycle of unconverted butane in the off-gas and recycle of recovered butane from the adsorption-desorption system.

Preferred catalysts for use in the present invention are high-activity, high-surface-area vanadium-phosphorus oxide catalysts, preferably having an intrinsic surface area between about 7 and 50 m$^2$/g.

Particularly preferred catalysts for use in the process of the present invention are those disclosed in Schneider U.S. Pat. No. 3,864,280, specifically crystalline phosphorus-vanadium mixed oxide catalysts containing pentavalent phosphorus, vanadium and oxygen, said vanadium having an average valence in the range from about +3.9 to +4.6, said oxide having a phosphorus-to-vanadium atomic ratio in the range from about 0.9–1.8 to 1, and an intrinsic surface area in the range from about 7 to 50 m$^2$/g.

As defined in the '280 patent, the term "intrinsic surface area" is used herein to mean the surface area of the mixed vanadium-phosphorus oxide material itself, i.e., per se, in the absence of a support or carrier.

The catalysts of U.S. Pat. No. 3,864,280 are particularly suited for use in the process of the present invention, and the disclosure of the '280 patent is incorporated herein by reference.

The process of the present invention is especially advantageous in that the catalyst of the '280 patent is not overoxidized and the "B-phase" of the catalyst is substantially retained during operation.

In the process of the present invention we have found that it is advantageous, especially in terms of obtaining long catalyst life of high selectivity, to maintain the oxygen concentration in the total feed gas to the reactor at about 6 to 12 volume percent, preferably 7 to 11 volume percent, and most preferably about 8 to 10 volume percent. To achieve this oxygen level, the air feed rate and/or the butane conversion level (within the stipulated ranges) and/or the fresh-feed butane content can be varied. The above oxygen concentrations have been found especially advantageous when used in conjunction with the preferred catalysts, i.e., the high-surface-area catalysts disclosed in the '280 patent.

The term "fresh butane" is illustrated by reference to FIG. 1, which shows the fresh or net butane feed to the process in line 1. The total butane fed to the reactor includes the fresh butane, the butane recovered from the reactor off-gas by adsorption (see line 16), and butane in the off-gas which is recycled directly to the reactor via line 3 without separating nitrogen, oxygen and carbon oxides from the off-gas.

As already indicated, the term "selectivity" is used herein to mean the weight percent of maleic anhydride obtained per pound of butane converted.

The selectivities herein are on a weight percent basis; the theoretical maximum selectivity is 169 weight percent if 1 mol of butane is converted entirely to maleic anhydride with no by-product formation.

In the present invention, whether air or a high oxygen content feed, such as purified oxygen or enriched oxygen, is used as the oxygen source, the oxygen content in the reactor total feed mixture can be adjusted by the amount of recycle to the reactor. In addition to use of the recycle to adjust oxygen concentration, an outside source of inert gas, such as nitrogen, argon or helium, can also be used to adjust the oxygen concentration.

According to the most preferred embodiments of the present invention, air is used as the sole oxygen source.

Where one simply wanted to take advantage of long catalyst life and high selectivity found by using the per pass conversion levels as specified herein, e.g., in an embodiment where there is an alternate use for the recovered n-butane or where recovery of n-butane is omitted altogether, such as when a portion of the off-gas is burned as fuel, an alternate embodiment of the invention may be defined in terms of the following improvement: In a process for producing maleic anhydride from n-butane wherein (a) n-butane is contacted with an oxygen-containing gas and a catalyst comprising vanadium-phosphorus oxides to thereby convert the butane to maleic-anhydride, (b) maleic anhydride is removed from the reactor effluent to obtain a maleic anhydride-lean off-gas, and (c) at least a portion of the off-gas is recycled to the reactor, the improvement is made which comprises maintaining the conversion level within the ranges previously stipulated herein, preferably between about 22 and 27% per pass.

Preferred selectivities and catalysts and operating temperatures and pressures for this alternate embodiment are as aforesaid for the preferred embodiment wherein air is used as the oxygen source and n-butane is recovered for recycle to extinction.

FURTHER DESCRIPTION OF THE DRAWINGS AND EXAMPLES

EXAMPLE 1

Figure 1:
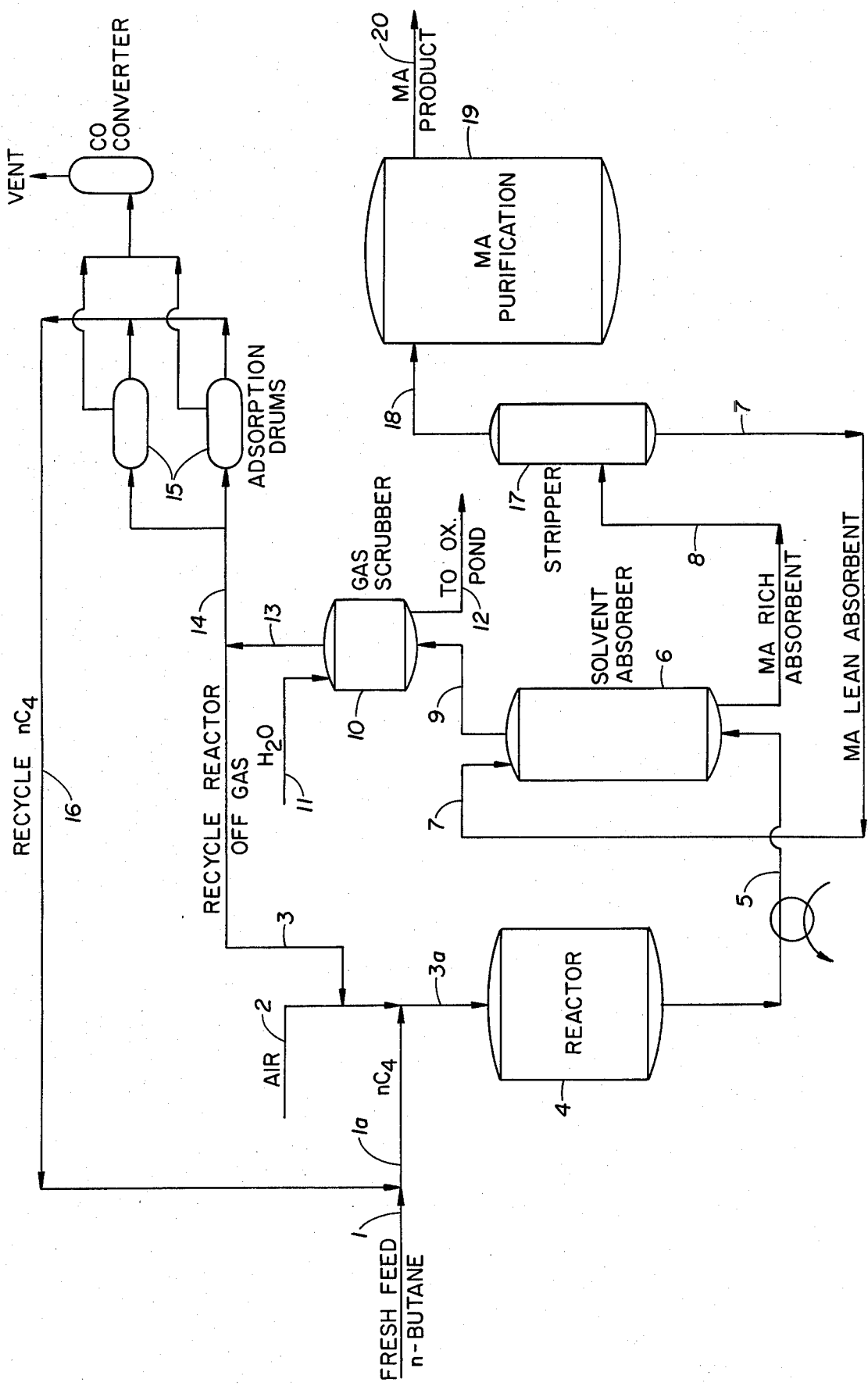
FIG. 1 is a schematic process flow diagram illustrating a preferred embodiment of the present invention.

Feed butane in line 1a, made up from 97 lbs/hr of fresh-feed butane in line 1 and 52 lbs/hr of recycled butane in line 16 is mixed with about 1426 lbs/hr of fresh make-up air introduced via line 2, and about 6379 lbs/hr of recycled off-gas from line 3 and the mixture is introduced into oxidizer reactor 4 through line 3a. The oxidizer reactor consists of conventional heat exchanger-type design with catalyst packed in tubes surrounded by a heat-transfer liquid (a "salt bath"). The reaction mixture is oxidized in the presence of a catalyst effective for accelerating the reaction of n-butane with air to form maleic anhydride. Preferred catalysts comprise mixed oxides of vanadium and phosphorus, especially those described in the previously cited U.S. Pat. No. 3,864,280, and preferred reaction temperatures are in the range 700°–800° F.

Following oxidation, the gaseous effluent flows through line 5 into absorber 6. About 104 lbs/hr of maleic anhydride is absorbed in the organic solvent flowing into the absorber from line 7. The gaseous stream, 7849 lbs/hr, leaves the absorber through line 9 at a temperature of about 160° F. and is given a water wash in vessel 10 and water soluble impurities are removed through line 12.

The solvent-maleic anhydride stream leaves the absorber through line 8 for maleic anhydride stripping in stripper 17. After stripping, maleic anhydride is taken from stripper 17 through line 18 and is passed into MA purification vessel 19, where it is purified, for example, by distillation. The final product is removed through line 20.

Washed off-gas leaving the water wash through line 13 and at a temperature of about 100° to 120° F. is split into streams 3 and 14. About 6379 lbs/hr of this washed off-gas is compressed and recycled back to the oxidizer through line 3 and the remaining 1385 lbs/hr of off-gas is passed through line 14 for butane recovery in adsorber 15.

Butane in line 14 is adsorbed in the adsorber by a cyclic operation using multiple beds filled with adsorbents such as activated carbon. The denuded off-gas, 1334 lbs/hr, mainly containing oxygen, nitrogen and oxides of carbon, is vented out and the butane adsorbed on the adsorbent is recovered by suitable desorption such as steaming at about 250° F. followed by condensation and phase separation. The recovered butane, 51 lbs/hr, is then recycled back through line 16 to the reactor.

EXAMPLE 2

Figure 2:
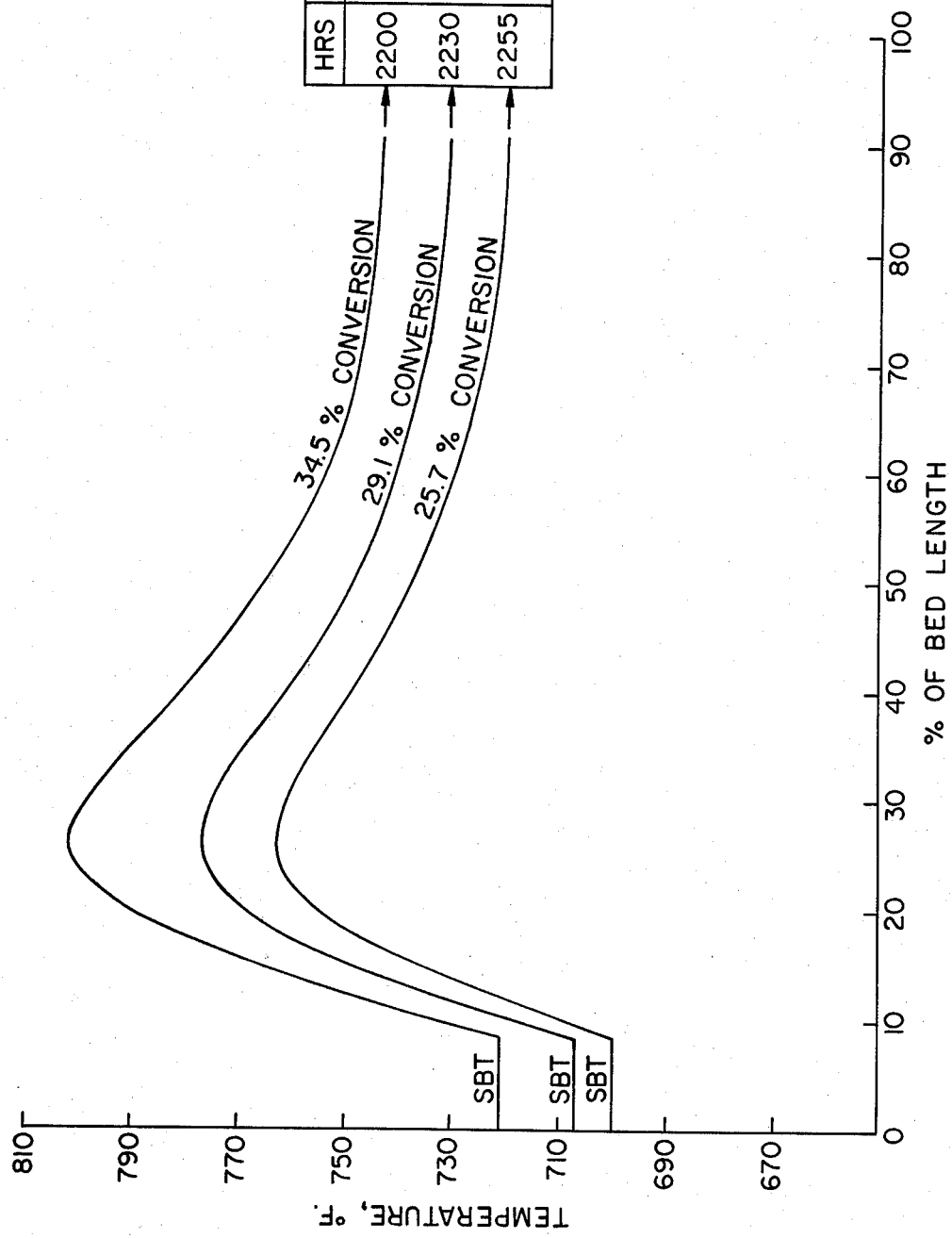
FIG. 2 shows a temperature profile for the reactor at various conversion levels.

The oxidizer, absorber and the recycle operations for off-gas and butane were carried out as in Example 1 in a pilot plant, but without recycle of butane recovered by adsorption. The temperature of the catalyst bed was measured by use of a set of thermocouples placed in an axial thermowell located at the center of one of the oxidizer tubes. A typical temperature profile along the catalyst bed normally showed an initial increase in the catalyst temperature in the first part of the catalyst bed, followed by a decrease in the temperature in the latter part of the bed. Typical profiles obtained at various operating conditions are shown in FIG. 2. In FIG. 2, the abscissa is the percent distance along the tube from the feed inlet, and the ordinate is the temperature recorded at that level. The three flat portions of the curves in the first 10% of the tube are the salt-bath temperatures (SBT).

The temperature of the heat-transfer liquid bath (SBT) was first dropped by about 14° F. from 721° F. to ascertain, among other factors, the effect of lower operating temperatures on the oxidizer operation. The decrease in the maleic anhydride production rate (productivity) due to such a temperature decrease was compensated for by increasing the butane feed rate. The temperature was next dropped to 700° F., and productivity was maintained as before by increase in butane feed rate. The temperature profiles of FIG. 2 thus represent the cumulative result of the two changes, i.e., salt bath temperature decrease and butane feed increase.

The axial temperature profile resulting from this lower per-pass conversion level was measured using the aforementioned set of thermocouples. The above procedure was repeated at three different per-pass conversion levels, at each time maintaining the maleic anhydride production rate at a constant value.

It will be seen that the position of the "hot spot" remains the same, but its temperature decreases with the changes. The response of the "hot-spot" temperature to a lowering of the salt-bath temperature is a greater drop in temperature, as tabulated in Table I.

TABLE I

| Salt-Bath Temperature, °F. | | | Hot-Spot Temperature, °F. | | |
|---|---|---|---|---|---|
| From | To | Change | From | To | Change |
| 721 | 707 | 14 | 802 | 777 | 25 |
| 707 | 700 | 7 | 777 | 763 | 14 |

In FIG. 2, the numbers in each column of Table II represent, sequentially, the following conditions for each of the three temperature runs: (1) total hours on the catalyst: (2) "X"=percent butane conversion per pass; (3) "Cin"=volume percent butane in the feed gas; (4) "Pr"=productivity (lbs maleic anhydride/cu.ft. catalyst/hour); (5) "Yo"=weight percent yield of maleic anhydride on an overall basis; and (6) "Z"=selectivity.

For convenience, Table II is also included at this point:

| HRS | X | Cin | Pr | Yo | Z |
|---|---|---|---|---|---|
| 2200 | 34.5 | 1.93 | 3.86 | 76.6 | 105 |
| 2230 | 29.1 | 2.08 | 3.79 | 75.3 | 110 |
| 2255 | 25.7 | 2.44 | 3.87 | 72 | 113.6 |

Referring to the values in Table II, it will be seen that as the salt-bath temperature is lowered from 721° to 707° to 700° F., the concentration of butane in the feed is increased from 1.93 to 2.08 to 2.44%. The increase in butane concentration was made to maintain productivity essentially constant; the productivity was maintained at about 3.86 pounds of maleic anhydride per cubic foot of catalyst volume per hour. However, the per pass conversion dropped from 34.5 to 29.1 to 25.7%.

At the same time, overall yields drop from 76.6 to 75.3 to 72 weight percent.

However, selectivity increased from 105 to 110 to 113.6 weight percent maleic anhydride, so that the ultimate yield of maleic anhydride per pound of fresh butane feed is 1.136, using the 25.7% conversion level in accordance with the process of the present invention, vs. 1.05 pounds maleic anhydride per pound of butane feed using the higher conversion level of 34.5% per pass, which is not in accordance with the present invention.

Thus, a comparison of the data obtained at 25.7, 29.1 and 34.5% per-pass conversion levels under these conditions shows our findings that: (a) higher ultimate process yields and selectivities are obtained at the indicated lower conversion levels of about 25% vs. 35%; and (b) substantial lowering and flattening of the axial temperature profile was achieved by operating the oxidizer at lower per-pass conversions, such as about 25%. Since a flat profile is indicative of a uniform work rate of the entire catalyst bed, such an operation is advantageous in terms of longer catalyst life at a given productivity.

Lower temperature differences between heat-exchanger bath temperature (salt-bath temperature) and the catalyst temperature were also found, and such, as well as the lower absolute catalyst bed temperature at the given productivity also helps assure a more stable and longer operation of the catalyst in the oxidizer.

A consequence of lower operating temperature and per-pass conversion levels found was that the useful life of the catalyst was extended a surprising amount. Operating the oxidizer at higher per-pass conversion levels such as 35% was found to result in about 3.5 times faster loss of catalyst selectivity than at lower conversion levels such as 25%.

For feed butane concentrations below about 5%, we have found that operation below about 15% conversion per pass is unattractive in terms of the resultant need to handle large recycle volumes and large butane recovery requirements for the adsorbers.

What is claimed is:

1. A process for producing maleic anhydride from n-butane which comprises:
   (a) feeding n-butane and air to a reactor;
   (b) contacting the butane and air in the reactor with a crystalline vanadium and phosphorus mixed oxide catalyst at reaction conditions including a temperature between 550° F. and 1000° F. so as to convert 15 to 28% of the butane per pass and obtain a reactor effluent containing maleic anhydride, unreacted butane, nitrogen, and oxygen, said catalyst consisting essentially of pentavalent phosphorus, vanadium and oxygen, said vanadium having an average valence in the range from about +3.9 to +4.6, said catalyst moreover having a phosphorus-to-vanadium atomic ratio in the range from about 0.9–1.8 to 1;
   (c) removing maleic anhydride from the reactor effluent to obtain maleic anhydride-lean effluent;
   (d) recycling a portion of the maleic anhydride-lean effluent to the reactor so as to maintain in the reactor an oxygen content of about 6–12 volume %;
   (e) removing butane from the other portion of maleic anhydride-lean effluent; and
   (f) recycling the removed butane to the reactor.

2. In a process for producing maleic anhydride from n-butane wherein (a) the n-butane is contacted with an oxygen-containing gas and a crystalline vanadium-phosphorus oxide catalyst thereby to convert the butane to maleic anhydride, said catalyst consisting essentially of pentavalent phosphorus, vanadium and oxygen, said vanadium having an average valence in the range from about +3.9 to +4.6, said catalyst moreover having a phosphorus-to-vanadium atomic ratio in the range from about 0.9–1.8 to 1, (b) maleic anhydride is removed from the reaction effluent to obtain a maleic anhydride-lean off-gas, and (c) at least a portion of the off-gas is recycled to the reactor, the improvement which comprises maintaining the conversion level between 15 and 28% per pass while maintaining the oxygen content in said oxygen-containing gas at about 6–12 volume %.

3. A process in accordance with claim 1 wherein the reaction conditions are adjusted to convert 22 to 27% of the butane per pass.

4. A process in accordance with claim 1 wherein the catalyst has a surface area between 7 and 50 $m^2/g$.

5. A process in accordance with claim 2 wherein the conversion level is maintained between 22 and 27% per pass.

* * * * *

UNITED STATES PATENT AND TRADEMARK OFFICE
CERTIFICATE OF CORRECTION

PATENT NO. : 4,231,943

DATED : Nov. 4, 1980

INVENTOR(S) : Stephen G. Paradis, David M. Marquis, Kiran R. Baksh

It is certified that error appears in the above-identified patent and that said Letters Patent are hereby corrected as shown below:

Col. 4, line 54, "C." should read --$C_4$--.
Col. 4, line 55, "C." should read --$C_4$--.

Signed and Sealed this

Seventh Day of July 1981

[SEAL]

Attest:

RENE D. TEGTMEYER

Attesting Officer    Acting Commissioner of Patents and Trademarks